United States Patent [19]

Lowell

[11] Patent Number: 5,360,743
[45] Date of Patent: Nov. 1, 1994

[54] METHOD FOR MEASURING A SAMPLE SORPTION AND A SAMPLE CELL VOID VOLUME AND WALL ADSORPTION USING AN ADSORBATE GAS

[75] Inventor: Seymour Lowell, Glenhead, N.Y.

[73] Assignee: Quantachrome Corp., Boynton Beach, Fla.

[21] Appl. No.: 114,370

[22] Filed: Sep. 1, 1993

Related U.S. Application Data

[62] Division of Ser. No. 850,455, Mar. 10, 1992, abandoned.

[51] Int. Cl.$^5$ .............................................. G01N 15/08
[52] U.S. Cl. ........................................ 436/5; 436/8; 73/38; 73/865.5; 73/1 R; 73/3
[58] Field of Search ................... 73/38, 865.5, 1 R, 3; 422/69, 88; 436/5, 8

[56] References Cited

U.S. PATENT DOCUMENTS

| | | | |
|---|---|---|---|
| 4,305,291 | 12/1981 | Nelson | 73/865.5 |
| 4,489,593 | 12/1984 | Pieters et al. | 73/38 |
| 4,496,249 | 1/1985 | Lee et al. | 374/7 |
| 4,762,010 | 8/1988 | Borghard et al. | 73/865.5 |
| 5,065,634 | 11/1991 | Jennings | 73/865.5 |
| 5,109,716 | 5/1992 | Ito et al. | 73/865.5 |

*Primary Examiner*—James C. Housel
*Assistant Examiner*—Jan M. Ludlow
*Attorney, Agent, or Firm*—Hopgood, Calimafde, Kalil & Judlowe

[57] ABSTRACT

A sorption analyzer for performing surface measurement analysis on sample material. The sorption analyzer calibrates the instrument and the sample cell using the adsorbate gas.

4 Claims, 9 Drawing Sheets

METHOD FOR MEASURING A SAMPLE SORPTION AND A SAMPLE CELL VOID VOLUME AND WALL ADSORPTION USING AN ADSORBATE GAS

This is a divisional application of U.S. application Ser. No. 07850,455, filed Mar. 10, 1992, now abandoned.

BACKGROUND OF THE INVENTION

1. Field of the Invention

The present invention relates generally to measurement techniques for performing adsorption and desorption gas analyses on materials. By employing the apparatus and method disclosed herein, the void volume is determined without the use of a non-adsorbable gas, such as helium. Unlike previous methods and apparatus, the adsorption of the sample cell walls are measured. By using the same gas that is used to calibrate the sample cell for measuring the adsorption and desorption properties of the samples, pressure—volume data points can be used to prepare adsorption and desorption isotherms, BET surface area, and other relevant information.

2. Description of the Prior Art

A great variety of applications in modern technology require accurate measurements concerning the microstructure of materials, such as powders. These materials are widely used, for example, as catalysts, or in the production of paint, cement, carbon blacks, absorbents, dessicants, and the like. The information desired regarding the microstructure of these materials includes the porosity and surface area of the powder as well as the distribution of pore volume in the various sized pores.

Many types of apparatus and systems have been developed for performing adsorption and desorption measurements on samples. All of these adsorption and desorption measurement systems have certain essential features. These include a non-adsorbable gas (e.g. helium) for calibrating the volume of the cell containing the sample, and an adsorbate gas for performing the adsorption analysis. The non-adsorbable gas is critical in these systems for calibrating the volume of the sample cell with the sample material present.

Errors in the existing methods of measurement arise principally from three sources. First, because a non-adsorbable gas is being used to calibrate the volume of the sample cell, the adsorption of the sample cell is not measured. Thus, when the adsorbate gas is subsequently introduced into the sample cell when it contains the sample, all of the gas adsorbed is assumed to be adsorbed by the sample itself. Any gas adsorbed by the cell walls is not considered. Therefore, the adsorption of the cell is not compensated for when measuring the adsorption of the sample. While this may be negligible when the surface area of the sample is high, the error increases as the surface area of a sample decreases and the amount of gas adsorbed by the cell wall is a greater fraction of the total gas adsorbed.

Second, when the sample cell is immersed in a coolant (for example, liquid nitrogen) often required for adsorption and for maintaining a constant temperature of the sample during the measurement process, the attained temperatures cause the adsorbate gas to deviate from the ideal gas law ($PV = nRT$). Therefore, the gas contained in the void volume of the sample cell which is cooled, must be corrected for deviations from ideality. However, because measurements are time consuming and must be made with precision, and because the void volume of the cell is not measured as accurately as desired, the amount of correction for the volume of the gas under non-ideal conditions is indeterminate. Attempts to resolve this problem in the past have focused upon minimizing, as much as possible, the amount of void volume in order to reduce the amount of error in the measurements. This has met with varying degrees of success.

The third source of error results from that portion of the sample cell located above the immersion bath. This portion of the sample cell is in a transition zone of non-uniform temperature ranging from the temperature of liquid nitrogen to the ambient temperature. This contributes to an ambiguous temperature zone which cannot be precisely determined and thus contributes to a further degree of error.

Further problems involving speed, cost, and difficulty in processing are related to using a non-adsorbable gas. Non-adsorbable gases, for example, helium, are expensive and add the need for a second gas with which to work. Additionally, they are expensive per unit volume, thereby increasing the cost of each measurement. Further, apart from not measuring the adsorption of the walls of the sample cell during calibration, it is time consuming to determine the volume of the sample cell each and every time a sample is to be measured in that sample cell.

There is therefore a great need in the art to correct for these major sources of errors in measuring the adsorption and desorption of a sample. Further, a method and apparatus to avoid these aforementioned sources of error and difficulties of measurement and to do so by using only the adsorbate gas itself has been heretofore unrealized.

Accordingly, there is now provided with this invention an improved apparatus and method for measuring the void volume, and the adsorption of the sample cell walls, and correcting for non-ideal gas behavior by using only the adsorbate gas. This present invention effectively overcomes the aforementioned difficulties and longstanding problems inherent in surface area and pore volume measurement. These problems have been solved in a simple, convenient, and highly effective way by which to increase the accuracy of the measurement and to decrease the time consumed in performing the measurement. Additional objects of the present invention will become apparent from the following description.

SUMMARY OF THE INVENTION

According to one aspect of the invention, an apparatus is provided for performing measurement analyses on a sample material. The apparatus comprises a sample cell for containing the sample and a manifold in communication with the sample cell for containing an adsorbate gas. In this apparatus, the adsorbate gas can be used for determining the void volume, the adsorption of the sample cell, and the adsorption of the sample. The apparatus also comprises a valve means interposed between the sample cell and the manifold for effecting fluid communication therethrough, a pressure sensing means in communication with the manifold for determining the pressure in the manifold and the sample cell, a temperature sensing means in communication with the manifold for determining the temperature in the manifold, and a vacuum means in communication with the manifold for evacuating the sample cell prior to performing the measurement analysis. The apparatus further comprises a microprocessor having a memory. The volume of the sample cell and the adsorption of the sample cell walls is stored in the memory so that when a measurement analysis is performed on a sample in the sample cell, the volume of the sample cell and the adsorption of the sample cell walls can be recalled from the memory.

As will be appreciated by those persons skilled in the art, a major advantage provided by the present invention is avoiding the need for a non-adsorbable gas for calibrating the sample cell void volume, i.e., that volume residing below the valve not occuppied by the sample material. It is therefore an object of this invention to use the same gas, that is, the adsorbate gas, to both calibrate the apparatus and the sample cell and to determine adsorption and desorption properties of a powder sample.

It is another object of the present invention to compensate for the amount of gas adsorbed by the sample cell walls.

It is a further object of the present invention to provide an apparatus which compensates for that portion of the sample cell in which the adsorbate gas deviates from non-ideality.

It is a still further object of the present invention to provide an apparatus which compensates for the portion of the sample cell at a non-uniform temperature.

It is still another object of the present invention to store the volume and adsorption of the sample cell in a memory of a microprocessor so that each sample cell need only be calibrated once.

The method and apparatus of the present invention will be better understood by reference to the following detailed discussion of specific embodiments and the attached figures which illustrate and exemplify such embodiments.

DESCRIPTION OF THE DRAWINGS

A specific embodiment of the present invention will be described with reference to the following drawings, wherein.

DESCRIPTION OF THE PREFERRED EMBODIMENT

The following preferred embodiment as exemplified by the drawings is illustrative of the invention and is not intended to limit the invention as encompassed by the claims of this application.

Figure 1:
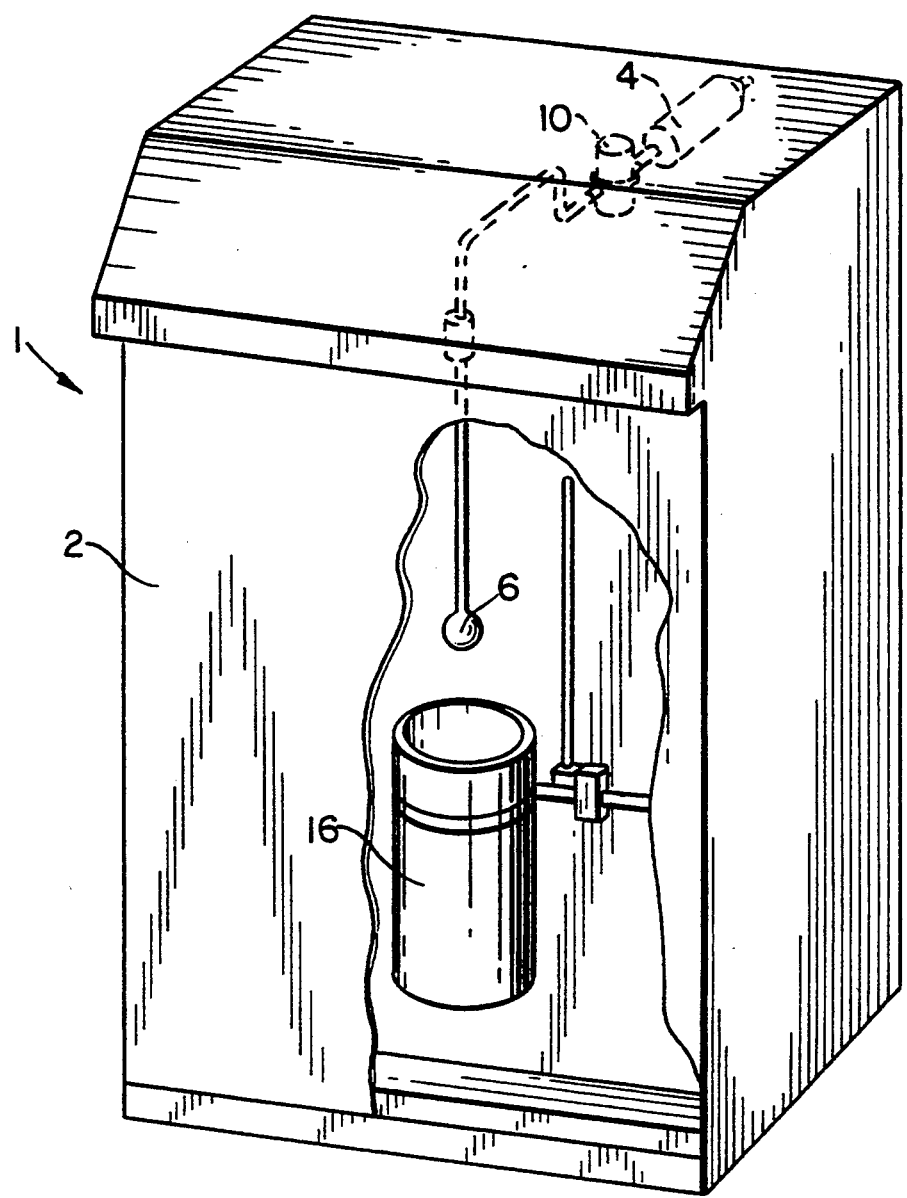
FIG. 1 is a perspective view of a sample analyzer in accordance with an embodiment of the present invention.

The apparatus of the invention, generally designated 1, as illustrated in FIG. 1, is contained within a housing 2. The housing 2 includes a manifold 4. A sample cell 6, which is adapted for containing a sample 8 to be measured, is in communication with the manifold 4. The manifold is adapted for containing any adsorbate gas, for example nitrogen, for conducting measurements of the sample 8. As shown schematically in FIG. 2, interposed between the sample cell 6 and the manifold 4 is a valve 10. The valve 10 effects fluid communication between the manifold and the sample cell for introducing the adsorbate gas into the sample cell when desired.

Figure 2:
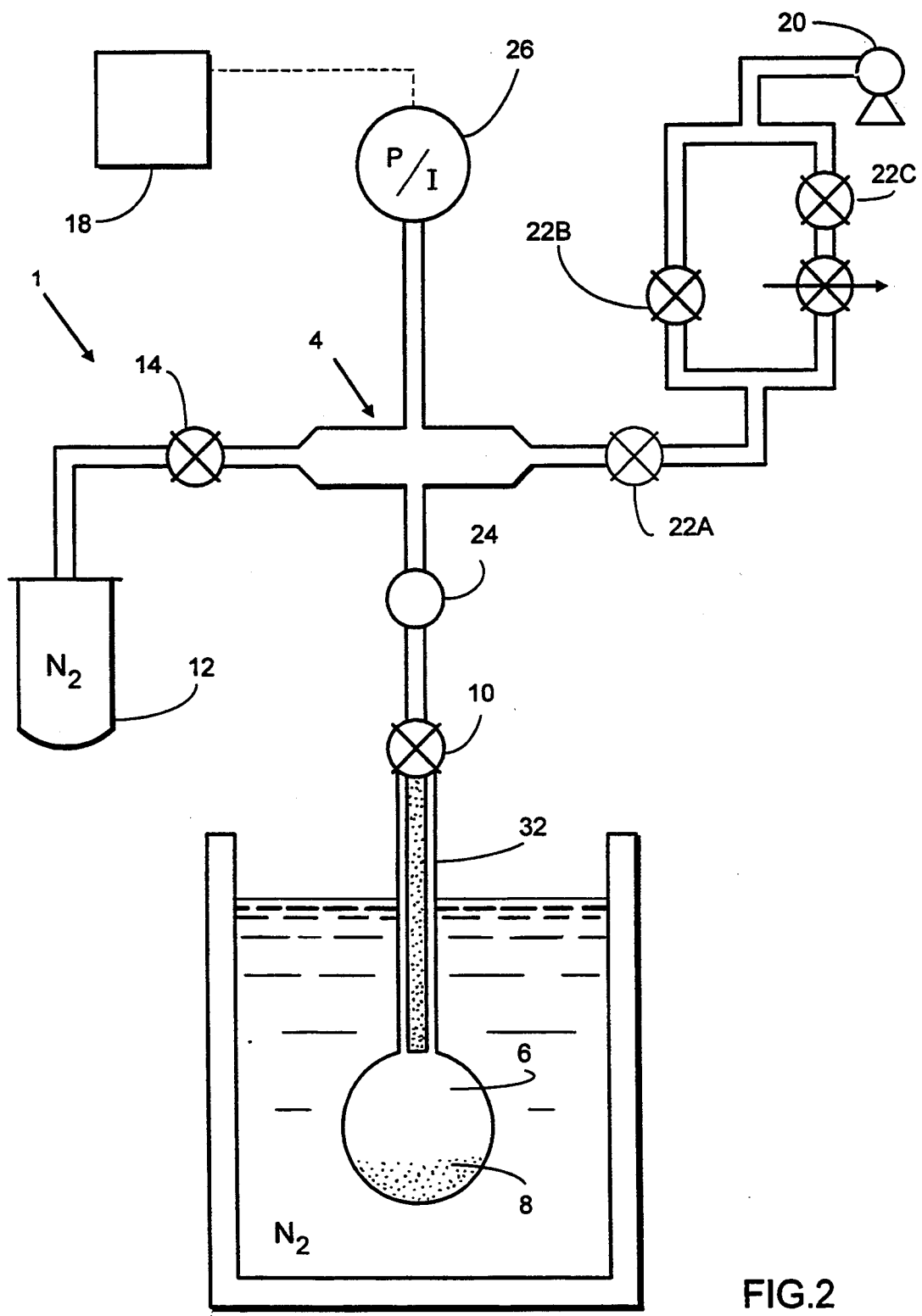
FIG. 2 is a schematic diagram of the apparatus of the present invention.
Figure 3:
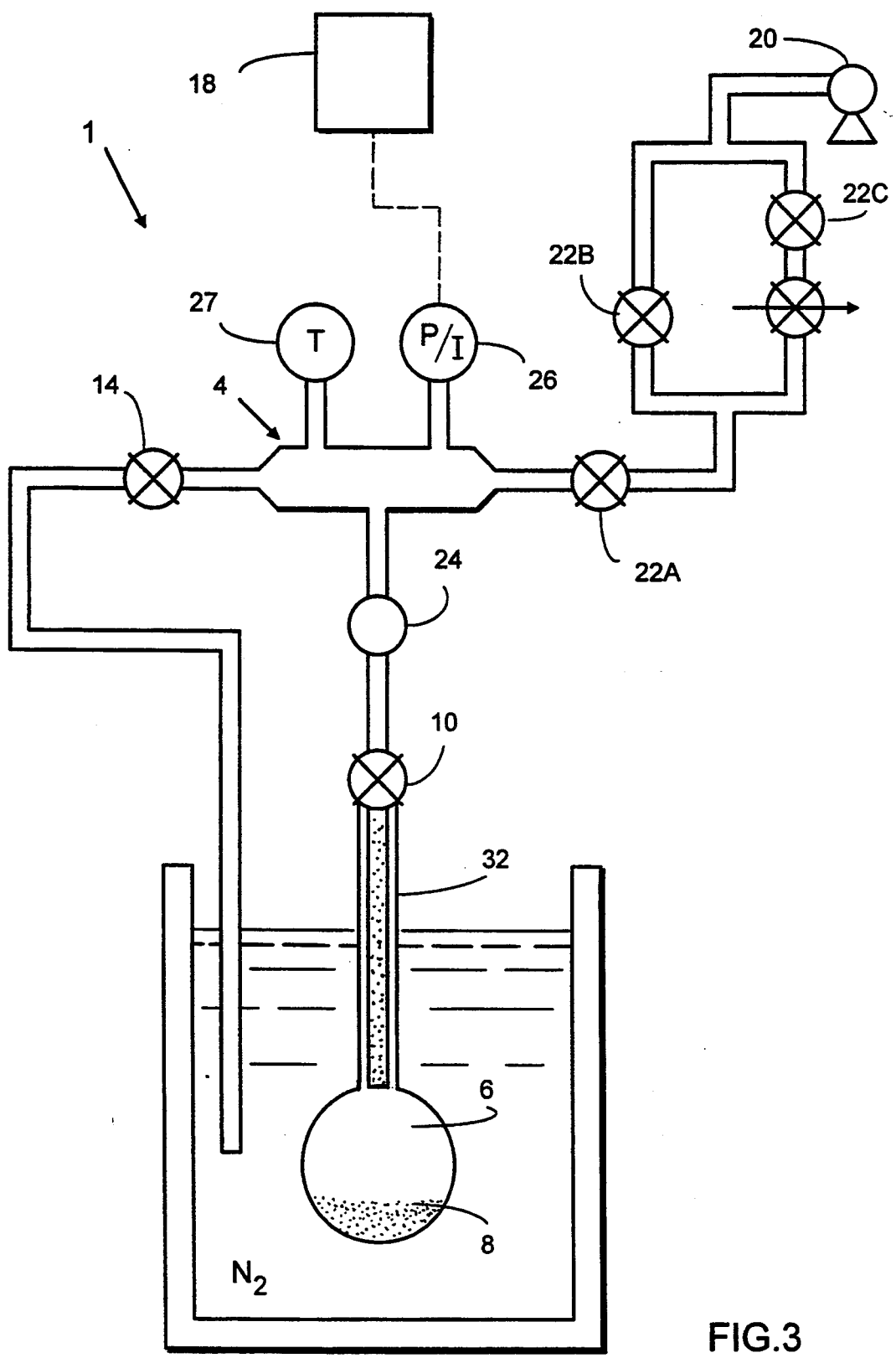
FIG. 3 is a schematic diagram of an alternate apparatus of the present invention.

In a preferred method of introducing the adsorbate gas into the manifold, as illustrated in FIG. 2, an adsorbate gas container 12 with a container valve 14 may be connected directly to the manifold 4, although alternate methods may also be employed. For example, the evaporated absorbate gas may be conducted from the coolant directly to the manifold. Such a connection is illustrated in FIG. 3.

As shown in FIGS. 1 and 2, positioned below the sample cell is a Dewar flask 16. The Dewar flask 16 is filled to an appropriate level with a coolant, for example, liquid nitrogen for maintaining an appropriate temperature of the sample in the sample cell during the measurement process. Positioned adjacent the housing 2 is a computer (microprocessor) and a data terminal 18. A monitor and a data printer-plotter (not shown) may also be included.

As described in greater detail below with respect to FIGS. 2, 4A, and 4B, the apparatus 1 is capable of calibrating the manifold and the sample cell as well as performing volumetric adsorption and desorption analyses of samples placed within the sample cell using the adsorbate gas. To this end, as depicted in FIG. 2, a vacuum source 20 may be preferentially coupled to the manifold by means of a plurality of isolation valves 22A–C. A septum 24 may also be interposed between the valve 10 and the manifold 4. If the septum 24 is employed, it may be used for quickly and easily dosing the manifold and the piping with a known quantity of gas for calibrating the manifold volume (Vm) of the apparatus 1 by injecting a known volume with a syringe through a septum. Alternatively, in place of the septum, a built-in plunger 25 may preferably be employed to introduce a known volume into the manifold to calibrate the manifold.

A pressure transducer 26 is coupled to the manifold 4 to measure manifold pressure and convert the measured pressure into a corresponding electrical signal. The programmed microprocessor 18 is electrically connected to the pressure transducer (by means of the broken line connections shown in FIG. 2) to receive the corresponding electrical signal. The microprocessor 18 transmits measurement and control signals to the valves.

Briefly, the analyzer unit of the invention, as illustrated in FIGS. 1 and 2, operates under the control of the microprocessor 18 in accordance with the program described below and with respect to FIGS. 4A and 4B. The program depicted in FIGS. 4A and 4B calibrates the apparatus and the sample cell and measures the quantity of gas adsorbed onto or desorbed from sample material placed within the sample cell at preselected equilibrium pressures. The data is obtained by admitting or removing a known quantity of adsorbate gas from the manifold into or out of the sample cell. As adsorption or desorption occurs, the pressure in the sample cell changes until an equilibrium pressure is established. The quantity of gas adsorbed or desorbed at the equilibrium pressure is the difference between the amount of gas admitted or removed, the amount of gas adsorbed by the sample cell walls, and the amount required to fill the space around the adsorbent, that is, the void space.

Figure 5:
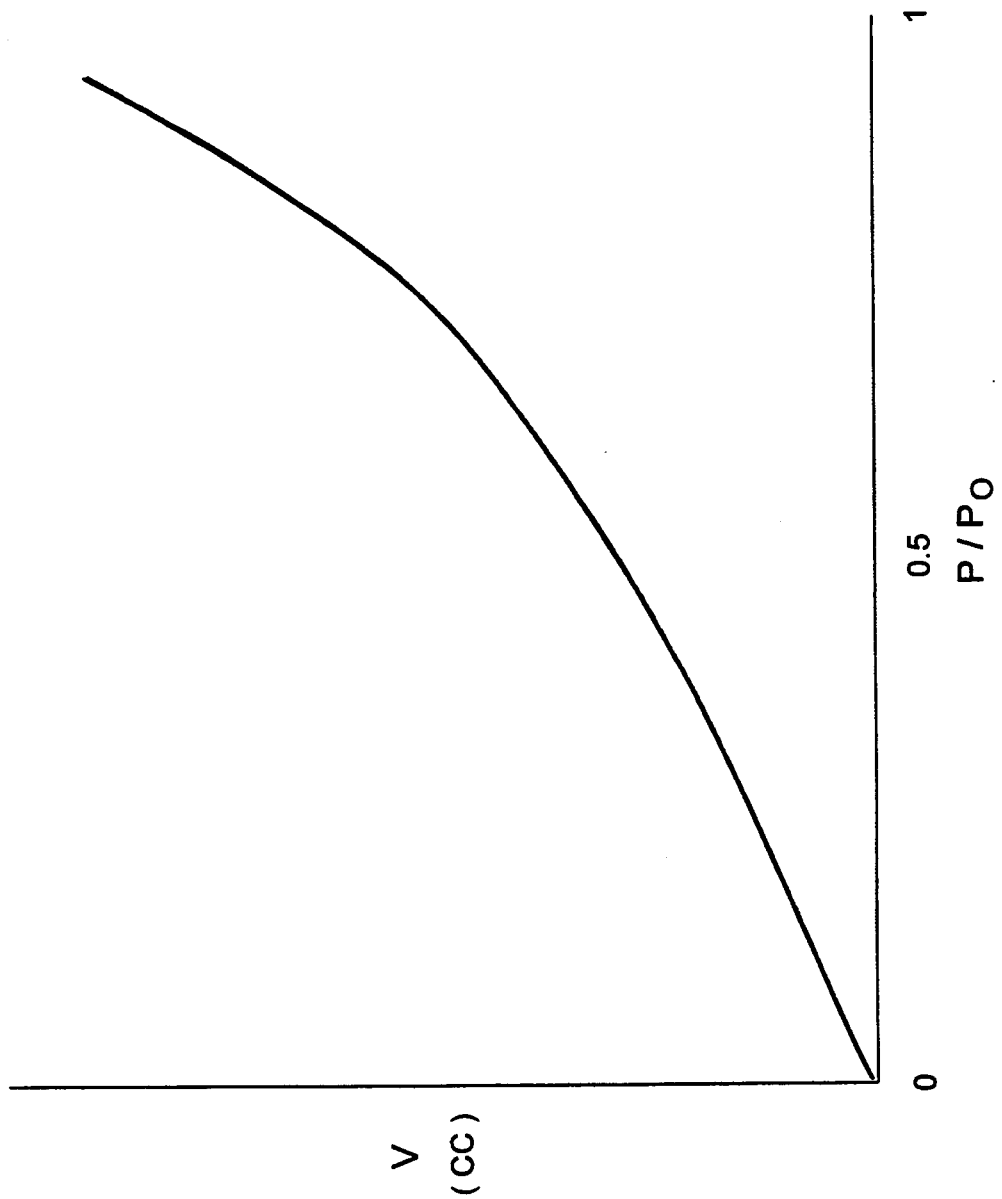
FIG. 5 is a typical calibration curve which can be determined by the present invention.
Figure 6:
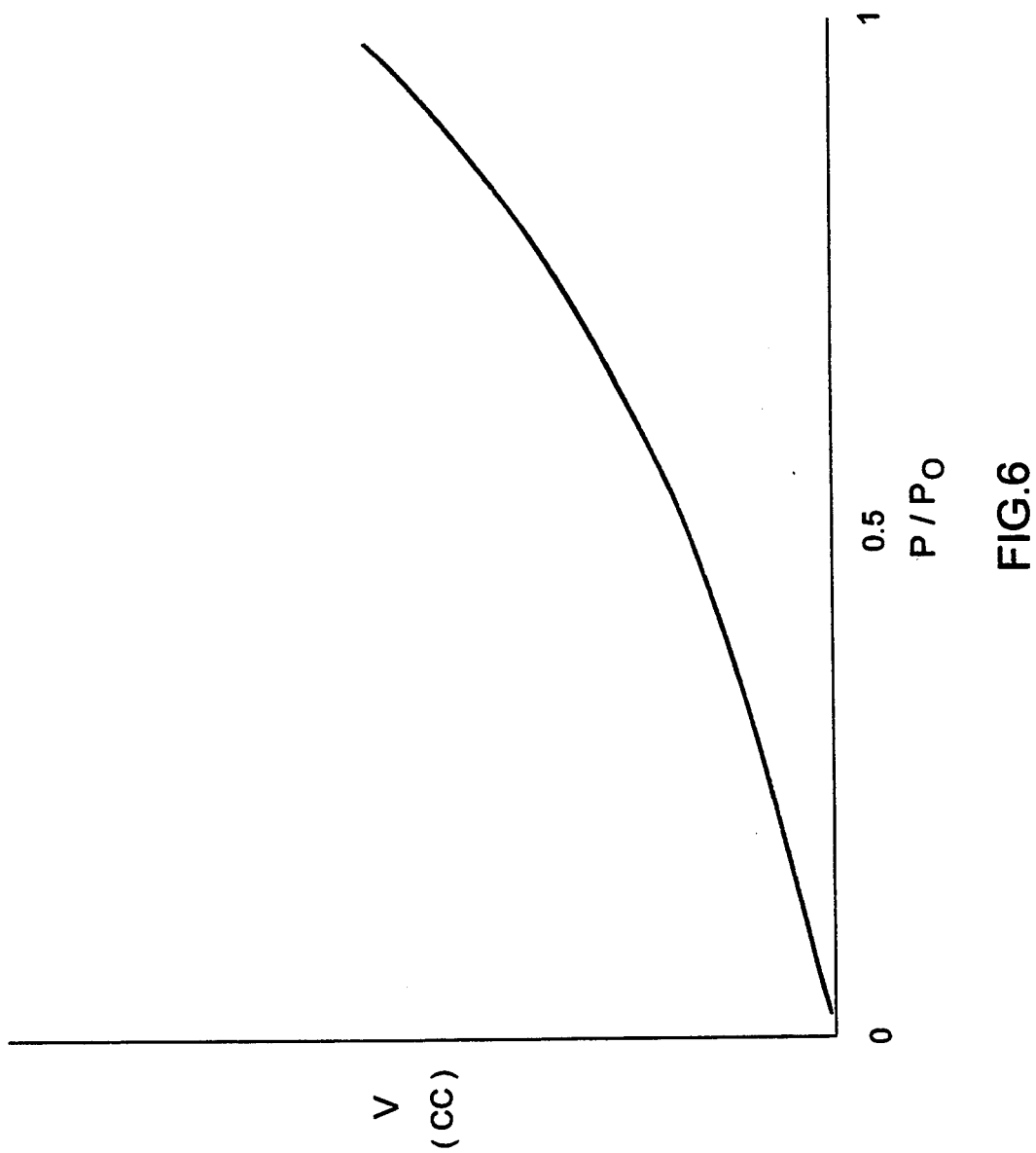
FIG. 6 is a second curve which is calculated by the present invention. The second curve represents what the curve of FIG. 5 would look like in the presence of sample material presuming that the sample material does not absorb any gas.
Figure 7:
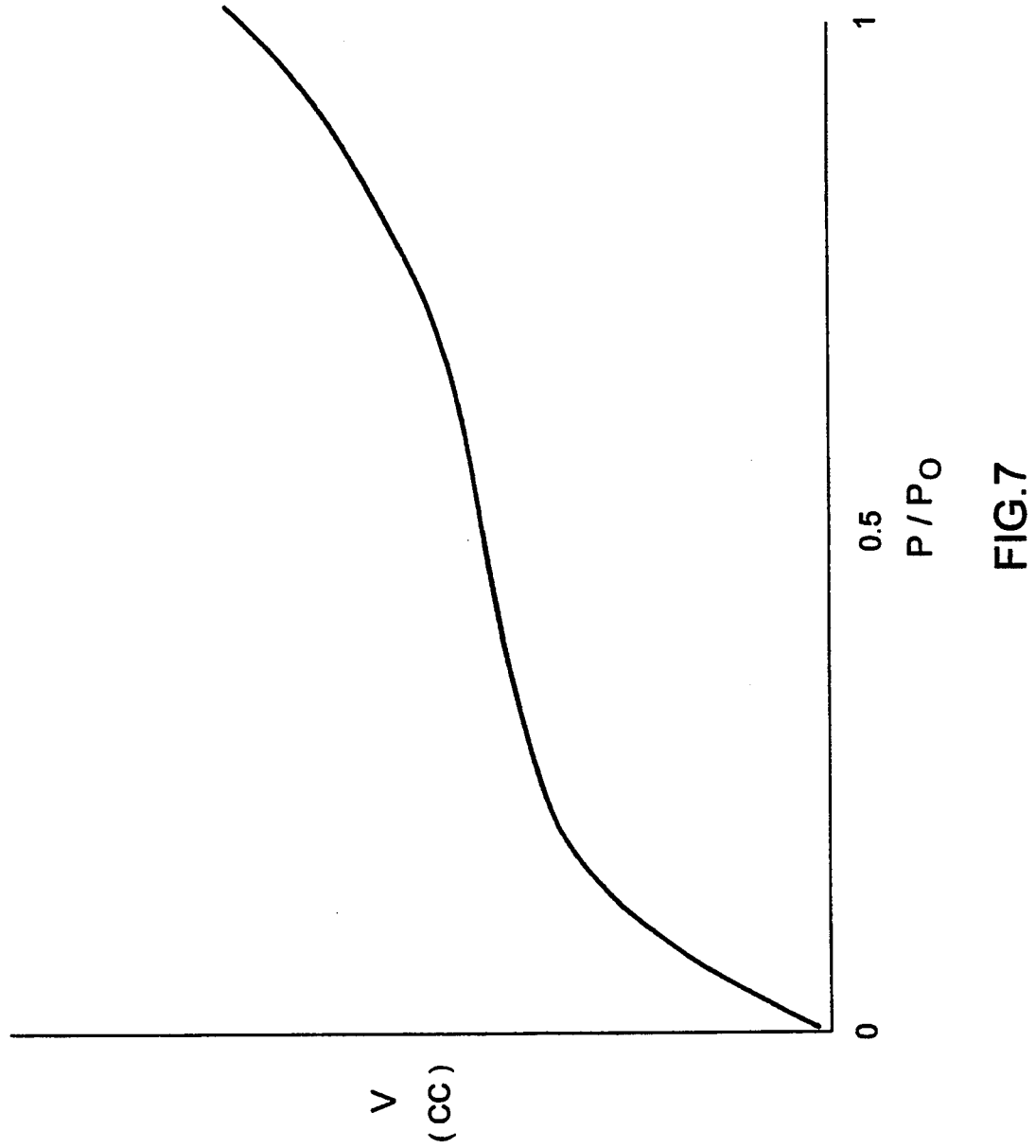
FIG. 7 is a typical adsorption—desorption isotherm which can be produced from the data obtained by the analyzer of the invention.

The volume—pressure data can then be processed to produce at a monitor (not shown), a first curve representing the amount of gas required to achieve a certain pressure in the sample cell plus the amount adsorbed by the sample cell, corrected for nonideality. FIG. 5 illustrates a typical first curve (a calibration curve) that can be produced at the monitor. When a known volume of sample material is subsequently added to the sample cell, a second curve is calculated from the first curve. This calculated curve (as illustrated in FIG. 6) represents the amount of gas that would have to be added to the sample cell in order to reproduce the points on the calibration curve, allowing for a change in the ideal gas correction due to the presence of a sample (which is assumed, for calculating purposes, to be non-absorbing) for that particular sample cell. Experimental volume—pressure data for the sample material is then produced. When the calculated curve is subtracted from the curve produced from the experimental volume—pressure data, the resultant curve (as illustrated in FIG. 7) represents an output with heretofore unrealized simplicity, accuracy, and speed. The output can then be used to produce the following well-known plots: a B. E. T. surface area plot, single point B. E. T. area, a Langmuir surface area plot, adsorption and/or desorption isotherms, pore size and surface area distributions, micropore volume and surface area using t-plots, and total pore volume and average pore radius. Such measurement is discussed generally in U.S. Pat. No. 4,566,326, which is incorporated herein by reference. For additional information concerning the B.E.T. (Brunauer, Emmett, and Teller) plot and the Langmuir surface area plot, see Introduction to Powder Surface Area by Seymour Lowell, Wiley—Interscience, 1979.

Figure 4A:
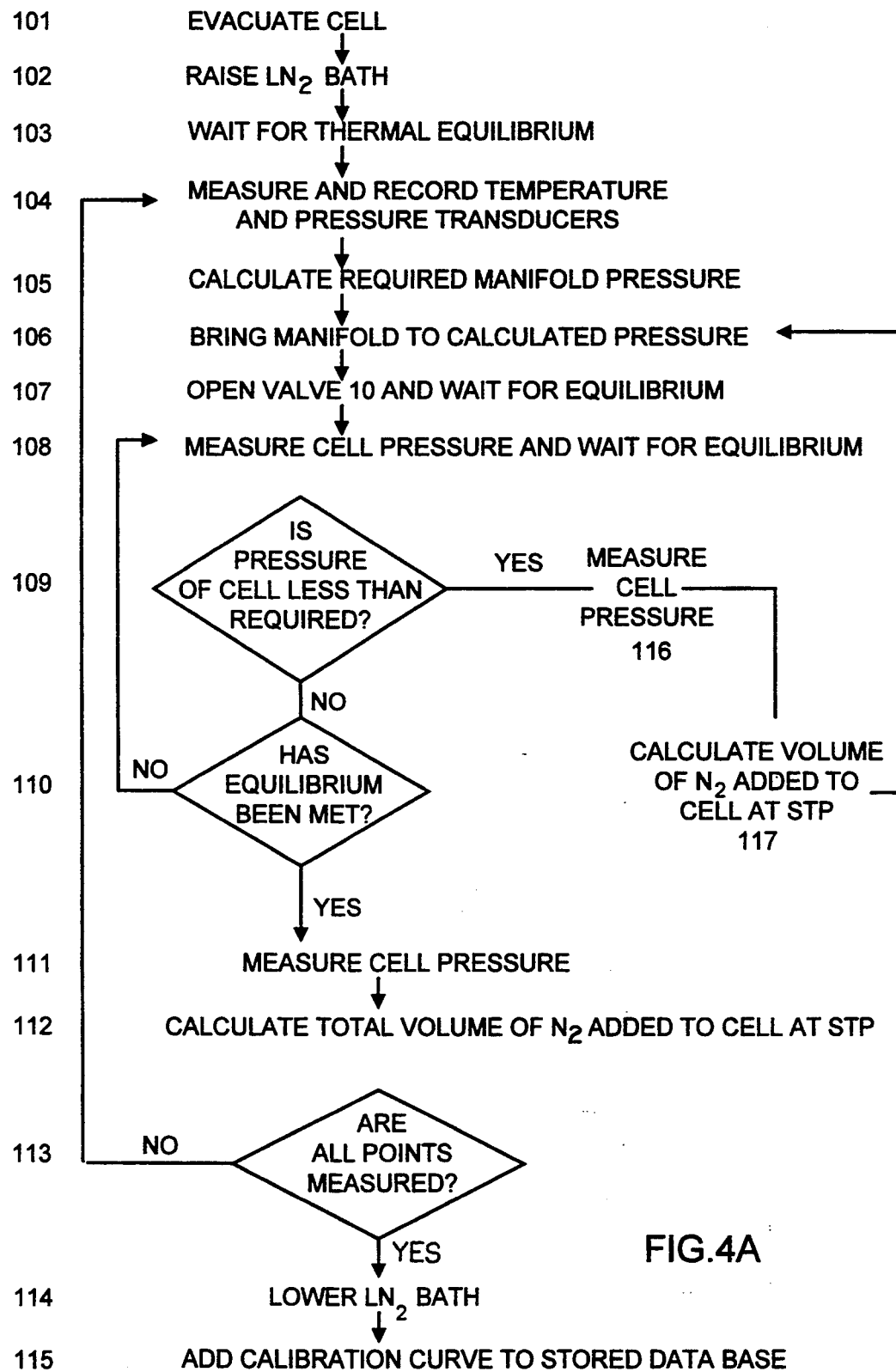
FIG. 4A is a flow chart of the program implemented in the microprocessor of the invention for calibrating the sample cell.
Figure 4B:
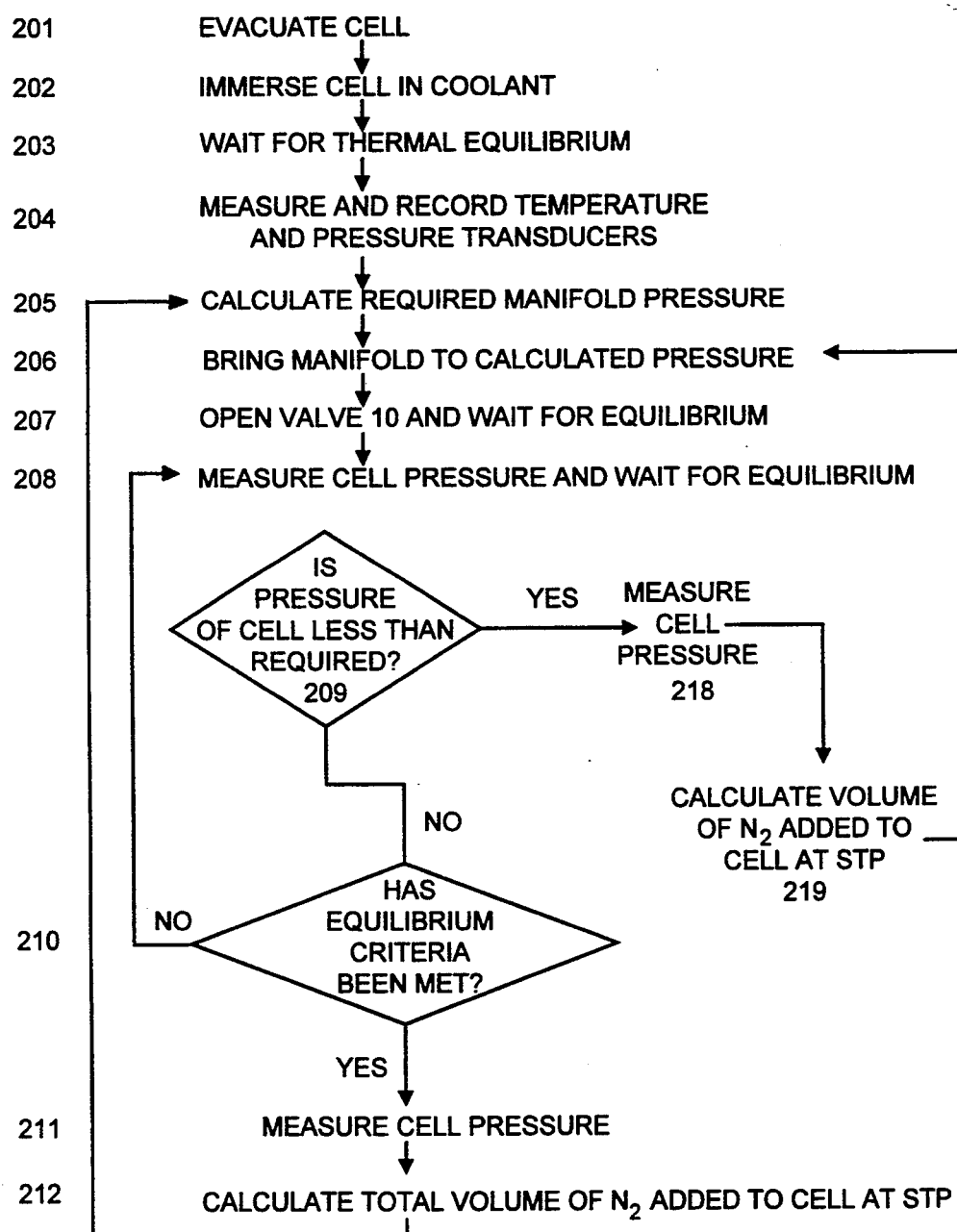
FIG. 4B is a flow chart of the program implemented in the microprocessor of the invention for calculating the calculated curve and for determines surface properties of the sample material.
Figure 4B:
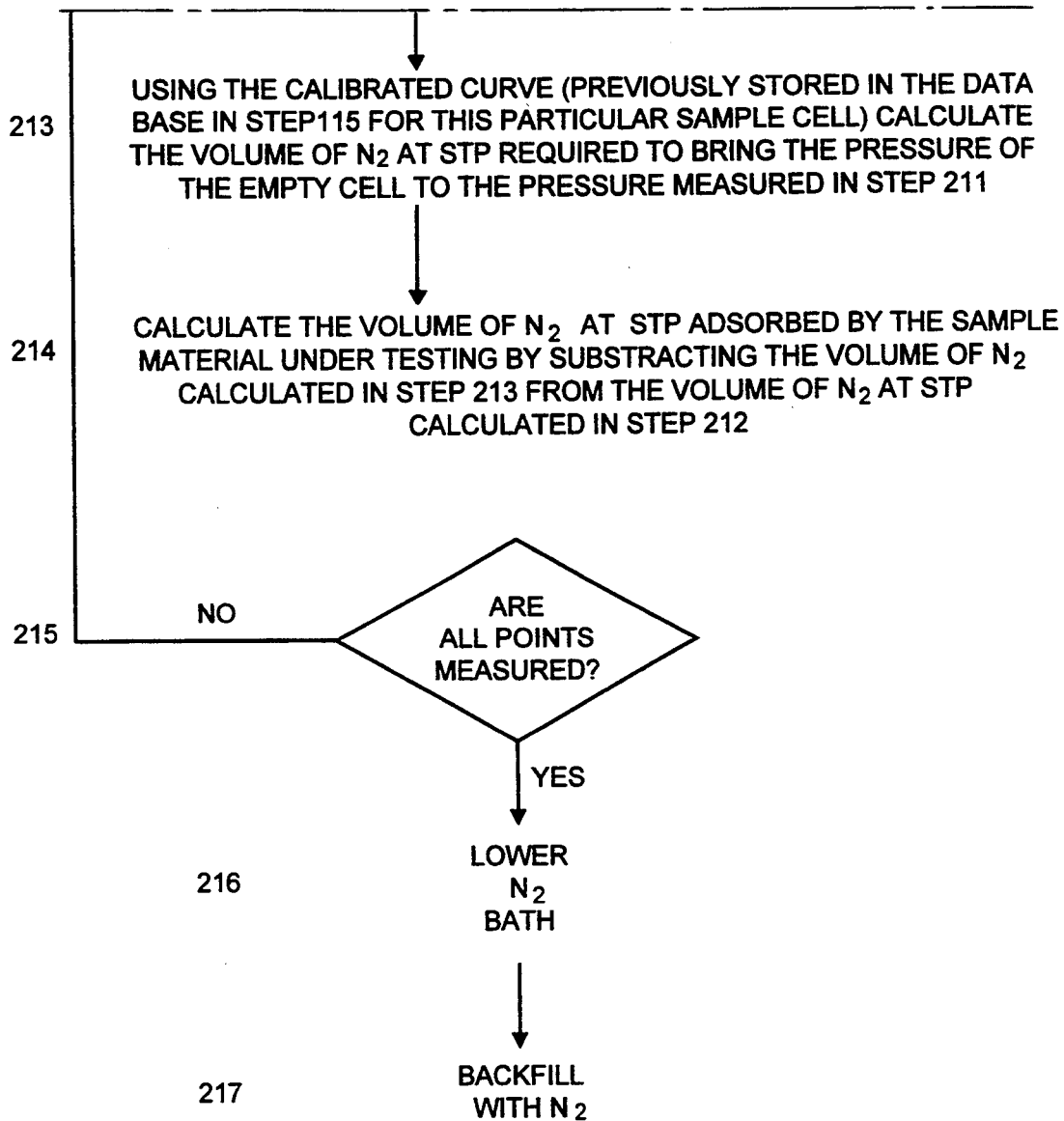

FIGS. 4A and 4B describe in a flow-chart form the steps carried out in calibrating the apparatus, calibrating the sample cell, and analyzing a sample in the sample cell. It is to be understood however, that although processing is described with regard to a single sample, and is in fact only performed on a single sample at any one instant in time, a plurality of sample cells may be simultaneously processed and processing of all or part of the calibration and measurement sequence can also be performed on a plurality of samples in a plurality of sample cells. Accordingly, during any given interval, all or part of a calibration or a sample analysis can be carried out on any number of sample cells or samples.

With respect to FIGS. 2, 4A, and 4B, before calibration of the analyzer or the sample cell, or analysis of sample material can commence, a leak test is performed to assure that there are no system leaks which would cause an error in measurement. Thereafter, the volume (Vm) of the manifold 4 is calibrated. The volume of the manifold does not have to be calibrated every time a sample cell is calibrated or every time a sample is measured. It need only be done, at the option of the operator, when a component in the system has been changed or when anything has been altered in the analyzer which would cause the manifold to deviate from a constant volume.

The first step is calibrating the manifold. If a syringe is used to calibrate the manifold as shown in FIG. 3, the manifold is first allowed to reach a known pressure. The syringe is introduced into a self-sealing septum 24 and a known volume of adsorbate gas is withdrawn from the manifold. The manifold and the syringe are then allowed to return to the known pressure. Thereupon, the manifold is isolated by closing the isolation valve 22A, the valve 10, and the container valve 14. The known volume contained in the syringe is then injected through the septum into the manifold. From the change in pressure sensed and transmitted by the pressure transducer 26, the manifold volume is measured and calibrated.

On the other hand, if the apparatus is equipped with a built in plunger 25, having a known volume as illustrated in FIG. 2, the manifold is allowed to reach a known pressure with the plunger 25 fully extended. The pressure is then noted by the computer. The plunger 25 is then depressed fully and a second pressure is noted by the computer. The volume of the manifold is then calculated. As aforementioned, unless there is a reason why the volume of the manifold has changed, this step in the process rarely needs to be done.

An empty sample cell is now calibrated. To this end, the overall volume and the adsorption of the sample cell walls is calculated from the measured changes in the volume of the manifold. A stem filler 32 of an inert substance, for example, glass, is inserted into the empty sample cell. The stem filler 32 is adapted to minimize the volume of the sample cell stem exposed to the adsorbate gas which would change temperature during analysis and, at the same time, allow fluid communication from the manifold into the entire sample cell. This fluid communication is effected by a small recess provided down the axial length of the stem filler. After the stem filler is inserted into the empty sample cell and the cell is in sealed fluid communication with the manifold. The Dewar flask 16 which contains the coolant, for example, liquid nitrogen, is raised so that the empty sample cell is immersed in the liquid nitrogen (step 102 in FIG. 4A). The volume of the cell immersed in the coolant is at a temperature of about 77.4° K. (when liquid nitrogen is employed). An empty cell calibration curve is now calculated for the empty sample cell.

This calibration curve is constructed in the following manner as shown in flow chart form in FIG. 4A. The empty sample cell is connected to the exit of the valve. The empty sample cell is dosed with the absorbate gas from the manifold until the required equilibrium pressure is achieved (step 103). By knowing the change in pressure associated with each dose from the manifold, and the temperature of the manifold which is constantly monitored with a thermocouple or thermistor probe, one can calculate the volume of gas at standard temperature and pressure required to bring the cell to a known constant pressure (steps 104, 105, and 106).

Such a calibration curve must be built one time for each and every sample cell which will be subsequently used for containing samples. A discrete calibration curve for each sample cell is stored in the microprocessor 18. By storing the volume and the adsorption of each sample cell as a calibration curve in the microprocessor, each sample cell need only be calibrated once. Thereafter, when a subsequent sample is placed in that sample cell for measurement and analysis, the calibration curve for that sample cell is recalled from memory before the subsequent sample material is tested.

The calibration curve for a sample cell is constructed as follows: The adsorbate gas is dosed into the empty sample cell at pre-selected relative pressure points assuming a preselected equilibrium vapor pressure (Po) (about 770 mm Hg for nitrogen). The preselected equilibrium vapor pressure (Po) is a function of both the adsorbate gas and the coolant contained in the Dewar flask. A preselected number of desired data points are then collected to calculate a calibration curve for the empty sample cell. This is shown in steps 107–117 in FIG. 4A. Because the empty sample cell is immersed in the coolant bath during this calibration procedure, the amount the adsorbate gas deviates from non-ideality is compensated for in the constructed calibration curve. Further, because the adsorbate gas is being used to calibrate the empty sample cell, any gas adsorbed by the cell itself is included in the curve and is therefore also compensated for in the calibrated curve which is constructed for each empty sample cell. FIG. 5 represents a typical calibration curve for an empty sample cell.

A known volume of the sample is then prepared for testing and analysis. This is shown in flow chart form in FIG. 4B. Before a sample can be analyzed, it is often necessary to remove contaminating materials which can alter the surface potential and block or fill pores. The preparation of the sample material is preferentially performed within the sample cell. The sample should preferentially be outgassed prior to the commencement of surface property measurements. Sample conditioning can be accomplished by vacuum pumping or purging with an inert gas. Both methods require the use of elevated temperatures to hasten the rate at which contaminants leave the surface. Caution must be used not to reach temperatures at which the sample properties can be altered. Melting, dehydration, sintering, and decomposition are processes which can drastically alter surface properties. Further, all air and contaminated materials which may have been entrained during transfer phases from outgassing instruments must be evacuated or purged from the cell. This can be done with or without the presence of a stem filler. If the sample material is subject to adsorbing contaminants, then it would be preferable to prepare the sample in the sample cell with the stem filler in place.

The sample cell containing the known volume of the prepared sample material is then connected to the exit portion of the valve 10 in the sample station. While the prepared sample is still warm, the sample cell is evacuated by the vacuum pump 20 (step 201 in FIG. 4B). The sample cell is then immersed into the coolant bath after inserting the stem filler (steps 202 and 203). The volume of the immersed portion of the cell is designated as the cold free space or cold void volume and is at a known temperature (for example, about 77.4° K. for liquid nitrogen). The remaining volume of the sample cell and the piping between it and the manifold, which are at ambient temperatures is designated as the warm free space or warm void volume. This warm free space is in a transition zone of an unknown temperature ranging from about 77.4° K. to the ambient temperature. By placing the known volume of the sample material into the sample cell, a second curve can be calculated for that particular sample cell containing the known volume of that particular sample. The calculated curve is theoretical, predicated on the theory that at this point, the known volume of the sample is non-adsorbing.

The calculated curve will always lie below the calibration curve because with a sample, less volume of gas is required to achieve a given pressure. This calculated curve represents the amount of adsorbate gas which would have to be dosed into that particular cell to reproduce the points on that sample cell's calibration curve in the presence of the known volume of that particular sample. FIG. 6 illustrates a typical calculated curve for a sample cell containing a known volume of sample. The calculated curve is determined from the calibration curve (step 213). The calculated curve compensates for the nonideality of the amount of adsorbate gas in the cold zone displaced by the sample volume, and any gas which is adsorbed by the cell walls. Since a calibration curve is stored in the microprocessor for each sample cell employed, as soon as the known volume of sample is added to a particular sample cell and is entered in the microprocessor, the calculated curve can immediately be determined.

Data must now be collected on the sample so that an experimental curve can be constructed representing the amount of gas adsorbed by the sample. Adsorbate gas is introduced to the sample by opening the valve 10 and allowing the gas to flow into the immersed sample cell. The system pressure is allowed to stabilize at preselected pressure values (steps 205–216). The amount the manifold pressure drops at each value at a known manifold temperature represents the amount of gas transferred to the sample cell. Following a series of iterative steps of allowing adsorbate gas to flow from the manifold to the cell, the manifold pressure and temperature is repeatedly measured before and after gas is allowed to flow to the cell.

The manifold pressure is controlled by the microprocessor with information provided by the pressure transducer. The temperature of the manifold can be either monitored or controlled, although monitoring is preferable. If the manifold temperature is monitored with a temperature transducer 27, then the measured temperature of the manifold is fed to the microprocessor electronically. Alternatively, if the manifold temperature is controlled, then a means of maintaining the temperature of the manifold is required, necessitating the need for additional hardware, such as a thermostat, and the microprocessor must have in its program the temperature at which the manifold is maintained.

The volume of adsorbate gas added or dosed into the sample cell is computed and that volume is added to any volume that had been previously computed during the iterative processing sequence. This experimentally determined volume represents the total volume of adsorbate gas introduced from the manifold volume to the sample cell containing the sample to achieve a desired data point and can be calculated as a volume at standard temperature and pressure. When the calculated curve is subtracted from the experimental curve, the difference between these two curves exactly represents the amount of gas adsorbed by the sample material. FIG. 7 illustrates a typical experimentally determined adsorption curve.

Thereafter, the true saturated vapor pressure (Po) may be measured. The term Po is defined as the saturated equilibrium vapor pressure exhibited by the pure adsorbate gas contained in the immersed sample cell. The temperature of the coolant is always found to deviate somewhat from the normal boiling point because of dissolved impurities from the atmosphere and because of ambient pressure fluctuations. Dissolved impurities usually increase the bath temperature sufficiently to cause the vapor pressure within the sample cell to increase above ambient pressure. For this reason, the saturated vapor pressure (Po) may be experimentally determined to correct for the previously preselected assumed value (about 770 mm Hg for nitrogen). To accomplish this, the sample cell may be pressurized to a pressure sufficiently high so as to cause the adsorbate gas to condense within the sample cell. Thus, the true saturated vapor pressure is determined. After condensation occurs, the equilibrium pressure in the sample cell is measured and the new experimentally determined equilibrium vapor pressure is substituted for the previously assumed value in the calculations. This substitution and Po measurement need only be performed if the utmost accuracy is desired.

As will be appreciated from the flow charts of FIGS. 4A and 4B, which illustrate the computation of an adsorption sequence, a desorption sequence follows essentially the same sequence of steps followed with the adsorbate gas being removed rather than being dosed into the sample cell. The relative pressures are then measured on a decreasing scale rather than on an increasing scale. Typically, the surface area of the sample material is measured by adsorption of the gas and the pore size of the sample material is measured by desorption of the gas. Although this measurement method is preferred, it is not required.

When data is measured on the desorption isotherm, the required relative pressure (P/Po) is initially set near unity, whereas in the derivation of adsorption data, the analysis begins with the sample under vacuum, or a relative pressure (P/Po) of near zero.

As described hereinabove, with respect to the flow charts of FIGS. 4A and 4B, the analyzer unit of the invention develops for each sample a series of values of adsorption or desorption volumes at a series of preset equilibrium pressures. These data points are fed to the computer 18 which, under the selection of the operator, can produce plots, printouts, or displays of the data in any one of a number of different useful forms including a complete adsorption-desorption isotherm, or a BET plot of the type shown in FIG. 6, the meaning of the symbols therein being the obvious one's, and which can be used to determine the surface area of the sample in a per se known manner. For a further explanation of the axes of the plots of FIG. 6, see *Introduction to Powder Surface Area*, by Seymour Lowell, Chapman and Hill, 1991, third ed.

The theory underlying the apparatus and method of the present invention is as follows:

Let N=moles of nitrogen gas transferred from a manifold of volume $V_m$ at temperature t(ambient) into an empty sample cell partly immersed in liquid nitrogen. Then:

$$N = N_c + N_w \quad (1)$$

where, $N_c$=moles transferred to the cell cold zone
$N_w$=moles transferred to the cell warm zone
Assuming ideal conditions:

$$\frac{\Delta P_m V_m}{Rt_{(amb)}} = \frac{\Delta P_c V_c}{Rt_c} + \frac{\Delta P_w V_w}{Rt_w} \quad (2)$$

Here, $\Delta P_m$ is the change in manifold pressure when gas is transferred to the cell. $\Delta P_w = \Delta P_c = \Delta P$ is the change in the pressure within the warm and cold zones of the sample cell. Because they are equal, equation (2) can be rewritten as:

$$\frac{\Delta P_m V_m}{Rt_{(amb)}} = \frac{\Delta P}{R} \left( \frac{V_c}{t_c} + \frac{V_w}{t_w} \right) \quad (3)$$

Although there exists a temperature gradient between the cold and warm zones of the sample cell, the volume of gas within the sample cell can be treated as though it was apportioned to a warm and cold zone with an infinitely steep gradient between zones, i.e., no intermediate temperatures, without introducing any error into these calculations.

Correcting equation (3) for non-ideality of the gas in the cold zone, yields:

$$\frac{\Delta P_m V_m}{Rt_{(amb)}} = \frac{\Delta P}{R} \left( \frac{V_w}{t_w} + \frac{V_c(1 + \alpha P)}{t_c} \right) \quad (4)$$

where P is the pressure within the cell and is the nonideality correction factor of $6.6 \times 10^{-5}$ torr$^{-1}$ for nitrogen.

When a sample is placed in the cell, the volume in the cold zone $V_c$ is reduced by the sample volume $V_s$ or $M_s \rho_s^{-1}$. $M_x \rho_s^{-1}$ are the sample's mass and density, respectively. Then, equation can be written as:

$$\frac{\Delta P_m V_m}{Rt_{(amb)}} = \frac{\Delta P}{R} \left( \frac{V_w}{t_w} - \frac{(V_c - M\rho^{-1})(1 + \alpha P)}{t_c} \right) \quad (5)$$

Solving equation (4) for the number of moles having the manifold N. required to achieve a specified cell pressure, yields:

$$N_a = \frac{\Delta P}{R} \left( \frac{V_w}{t_w} - \frac{V_c(1 + \alpha P)}{t_c} \right) \quad (6)$$

and similarly, the number of moles leaving the manifold to achieve the same cell pressure when a sample is present but no adsorption occurs, is given by:

$$N_B = N_a - \frac{\Delta P}{R} \left( \frac{V_w}{t_w} - \frac{(V_c - M\rho^{-1})(1 + \alpha P)}{t_c} \right) \quad (7)$$

Subtracting equation (6) from equation (7) yields $$N_B = N_a - \frac{\Delta P}{R} \frac{(M\rho^{-1})(1 + \alpha P)}{t_c)} \quad (8)$$

Rewriting equation (8) for the corresponding gas volumes at standard temperature and pressure (STP), yields:

$$V_B = V_a - \Delta P\, Mp^{-1} (1 + \alpha P) \frac{273.16}{77.4} \quad (9)$$

where 77.4 is the standard boiling point of liquid nitrogen.

A curve corresponding to equation (6) is stored in memory (the calibration curve) and corresponds to the volume of gas required to bring the sample cell to the required pressure and to the volume of gas adsorbed on the empty sample cell walls. When the known sample volume, or its density and mass is entered into the computer, the curve corresponding to equation (9) is calculated (the calculated curve). If these curves are called calibration curve and the calculated curve respectively, the calibration curve is preferentially constructed using 25 data points and the calculated curve values are therefore preferentially also every 0.04 fraction of the pressure axis.

When actual adsorption data is obtained, the corresponding value on the calculated curve is subtracted, thus yielding the experimental curve; adsorption or desorption data compensated for non-ideal gas behavior of only the gas volume in the cold zone of the sample cell allowing for the sample volume and also compensated for adsorption of the cell walls.

When subtracting the calculated curve from the actual adsorption data, the computer preferentially interpolates the data so that the subtraction is performed at exactly the same pressures.

Once obtained, the calibrated curve for any cell is permanently retained in memory until recalibrated with a new curve. Thereafter, the user need only enter the sample's volume, or mass and density in order to calculate a new calculated curve. This is done automatically as adsorption or desorption data is acquired.

Other data plots and printouts that can be produced from the pressure-volume data points obtained for one or more of the test samples processed include Langmuir plots, mesopore volume and surface area distributions, micropore volume and surface areas, total pore volumes, average pore radius, and many other calculations based on theories of surface chemistry. The processing of the raw data and the production of the printouts and plots for the sample in one of the sample cells may be carried out while processing continues on samples in the other cells or the one for which data is being processed.

It will be appreciated from the foregoing description of the invention that such data and printouts that characterize the sample material in the cell can be concurrently and independently obtained for a plurality of such samples.

Although the particular embodiments shown and described above will prove to be useful in many applications in the art of surface property measurement to which the present invention pertains, further modifications of the present invention herein disclosed will occur to persons skilled in the art, all such modifications are deemed to be within the scope and spirit of the present invention as defined by the appended claims.

I claim:

1. A method of measuring surface properties of a sample by measuring the volume of absorbate gas adsorbed by the sample contained in a sample cell by using only an adsorbate gas, in an apparatus having a manifold, comprising the steps of:

a. immersing a portion of an empty sample cell in a coolant;

b. determining a plural point, pressure versus volume calibration curve for compensating for the non-ideality of the adsorbate gas and for adsorption of the empty sample cell, by dosing said immersed empty sample cell with a plurality of volumes of the adsorbate gas and measuring corresponding sample cell pressures;

c. removing said empty sample cell and introducing a known volume of the sample into said sample cell;

d. determining a second curve calculated from said calibration curve and said known volume of the sample, wherein said second curve provides the amount of adsorbate gas which would have to be dosed into said sample cell containing the sample to reproduce said calibration curve;

e. determining a plural point, volume versus pressure, experimental curve, wherein said experimental curve provides the amount of gas adsorbed, by reimmersing said sample cell containing the sample in the coolant and dosing said sample cell containing the sample with a plurality of volumes of the adsorbate gas and measuring corresponding sample cell pressures; and f. determining the amount of adsorbate gas adsorbed by the sample by subtracting said amount of adsorbate gas provided by said second curve from said amount of gas adsorbed provided by said experimental curve, wherein said determined amount of adsorbate gas adsorbed by the sample is compensated for by the amount of gas adsorbate adsorbed by said sample cell, and for non-ideality of the adsorbate gas.

2. The method of claim 1, further comprising determining said calibration curves for a plurality of known sample cells and storing said curves in a memory of said apparatus such that when properties of a sample are to be measured in a known sample cell, said second curve is determined from said stored calibration curve for that known sample cell.

3. The method of claim 1, further comprising introducing the adsorbate gas into said sample cell at a pressure sufficient to cause condensation within said sample cell so that a true equilibrium vapor pressure is determined.

4. A method of measuring surface properties of a sample by measuring the volume of adsorbate gas adsorbed by the sample contained in a calibrated sample cell having a calibration curve associated therewith using only an adsorbate gas, in an apparatus having a manifold, comprising:

a. introducing a known volume of the sample into the calibrated sample cell;

b. determining a curve calculated from the calibration curve and said known volume of the sample, wherein said calibration curve is a plural point, pressure versus volume calibration curve for compensating for the non-ideality of the adsorbate gas and for adsorption of the empty sample cell obtained by dosing the empty sample cell with a plurality of volumes of the adsorbate gas and measuring corresponding sample cell pressures while said sample cell is immersed in a coolant, and said calculated curve provides the amount of adsorbate gas which would have to be dosed into the calibrated sample cell containing the sample to reproduce the calibration curve;

c. determining a plural point, volume versus pressure experimental curve, by immersing the calibrated sample cell containing the sample in said coolant and dosing the calibrated sample cell containing the sample with a plurality of volumes of the adsorbate gas and measuring corresponding sample cell pressures, wherein said experimental curve provides the amount of gas adsorbed; and d. determining the amount of adsorbate gas adsorbed by the sample by subtracting the amount of adsorbate gas provided by said calibrated curve from the amount of gas adsorbed provided by said experimental curve, wherein said determined amount of adsorbate gas adsorbed by the sample is compensated for by the amount of adsorbate gas adsorbed by the calibrated sample cell, and for non-ideality of the adsorbate gas.

* * * * *